(12) United States Patent
Xu et al.

(10) Patent No.: US 11,191,425 B2
(45) Date of Patent: Dec. 7, 2021

(54) FLEXIBLE SURGICAL INSTRUMENT SYSTEM

(71) Applicant: BEIJING SURGERII TECHNOLOGY CO., LTD., Beijing (CN)

(72) Inventors: Kai Xu, Beijing (CN); Shu'an Zhang, Beijing (CN); Huichao Zhang, Beijing (CN); Tianlai Dong, Beijing (CN); Zhengchen Dai, Beijing (CN); Jiangran Zhao, Beijing (CN); Zhaoyu Zhang, Beijing (CN); Huan Liu, Beijing (CN)

(73) Assignee: BEIJING SURGERII TECHNOLOGY CO., LTD., Beijing (CN)

( * ) Notice: Subject to any disclaimer, the term of this patent is extended or adjusted under 35 U.S.C. 154(b) by 401 days.

(21) Appl. No.: 16/329,750

(22) PCT Filed: Aug. 31, 2017

(86) PCT No.: PCT/CN2017/099918
§ 371 (c)(1),
(2) Date: Feb. 28, 2019

(87) PCT Pub. No.: WO2018/041218
PCT Pub. Date: Mar. 8, 2018

(65) Prior Publication Data
US 2019/0208989 A1    Jul. 11, 2019

(30) Foreign Application Priority Data

Aug. 31, 2016  (CN) .......................... 201610797612.7
Aug. 31, 2016  (CN) .......................... 201610798123.3

(51) Int. Cl.
*A61B 17/00* (2006.01)
*A61B 34/30* (2016.01)
(Continued)

(52) U.S. Cl.
CPC ............ *A61B 1/0055* (2013.01); *A61B 1/008* (2013.01); *A61B 1/0052* (2013.01);
(Continued)

(58) Field of Classification Search
CPC ... A61B 34/70; A61B 31/71; A61B 2034/715; A61B 2034/301–306; A61B 17/00234;
(Continued)

(56) References Cited

U.S. PATENT DOCUMENTS 5,710,870 A * 1/1998 Ohm .......................... B25J 3/04
                                                          700/245
2011/0290856 A1  12/2011 Shelton, IV et al.
(Continued)

FOREIGN PATENT DOCUMENTS

CN  101200068 A  6/2008
CN  103085083 A  5/2013
(Continued)

OTHER PUBLICATIONS

State Intellectual Property Office of the People's Republic of China, First Search Issued in Application No. 201610797612.7, dated Mar. 14, 2018, 4 pages.
(Continued)

*Primary Examiner* — Katherine H Schwiker
(74) *Attorney, Agent, or Firm* — McCoy Russell LLP

(57) ABSTRACT

Disclosed is a flexible surgical instrument system, comprising a distal structural body comprising at least one distal structural segment each comprising a distal fixing disk and structural backbones; a proximal structural body comprising at least one proximal structural segment each comprising a
(Continued)

proximal fixing disk, structural backbones and driving backbones; a plurality of cable pulling mechanisms operable to convert a rotational motion into a linear motion to turn the at least one proximal structural segment; and a driving unit to input the rotational motion to the plurality of cable pulling mechanisms; the driving unit comprises: a plurality of driving shafts operable to transfer the rotational motion to the plurality of cable pulling mechanisms, and a first end of each of the plurality of driving shafts is connected with each of the plurality of cable pulling mechanisms.

19 Claims, 14 Drawing Sheets

(51) Int. Cl.
*A61B 1/005* (2006.01)
*A61B 1/00* (2006.01)
*A61B 1/008* (2006.01)
*A61B 34/00* (2016.01)

(52) U.S. Cl.
CPC ........ *A61B 1/0057* (2013.01); *A61B 1/00087* (2013.01); *A61B 17/00234* (2013.01); *A61B 34/70* (2016.02); *A61B 34/71* (2016.02); *A61B 1/00147* (2013.01); *A61B 2034/301* (2016.02); *A61B 2034/305* (2016.02); *A61B 2034/306* (2016.02)

(58) Field of Classification Search
CPC ............................... A61B 2017/00323; A61B 2017/003205–00314; A61B 2017/00327; A61B 2017/00318; A61B 2017/003; A61B 1/005–0057
See application file for complete search history.

(56) References Cited

U.S. PATENT DOCUMENTS

| 2013/0090763 | A1* | 4/2013 | Simaan | A61B 5/11 |
| --- | --- | --- | --- | --- |
| | | | | 700/258 |
| 2014/0090506 | A1 | 4/2014 | Tobey | |
| 2014/0330432 | A1* | 11/2014 | Simaan | A61B 34/35 |
| | | | | 700/250 |
| 2015/0352728 | A1 | 12/2015 | Wang | |
| 2016/0135914 | A1* | 5/2016 | Isoda | A61B 34/72 |
| | | | | 606/130 |

FOREIGN PATENT DOCUMENTS

| CN | 103315781 | A | | 9/2013 |
| --- | --- | --- | --- | --- |
| CN | 103340731 | A | | 10/2013 |
| CN | 103707322 | A | | 4/2014 |
| CN | 103948435 | A | * | 7/2014 |
| CN | 103948435 | A | | 7/2014 |
| CN | 104758013 | A | | 7/2015 |
| CN | 104883991 | A | | 9/2015 |
| CN | 205219114 | U | | 5/2016 |
| CN | 106236272 | A | | 12/2016 |
| CN | 106308938 | A | | 1/2017 |
| EP | 2008594 | A2 | | 12/2008 |
| WO | 2006060775 | A3 | | 6/2006 |
| WO | 2009094670 | A1 | | 7/2009 |
| WO | 2015126752 | A1 | | 8/2015 |

OTHER PUBLICATIONS

State Intellectual Property Office of the People's Republic of China, Office Action and Search Report Issued in Application No. 201610798123.3, dated May 30, 2018, 9 pages.
European Patent Office, Supplementary European Search Report Issued in Application No. 17845520.0, dated Mar. 23, 2020, Germany, 2 pages.
ISA State Intellectual Property Office of the People's Republic of China, International Search Report Issued in Application No. PCT/CN2017/099918, dated Nov. 29, 2017, WIPO, 4 pages.

* cited by examiner

FLEXIBLE SURGICAL INSTRUMENT SYSTEM

CROSS REFERENCE TO RELATED APPLICATIONS

The present patent application is a U.S. National Phase of Chinese International Application No. PCT/CN2017/099918 entitled "FLEXIBLE SURGICAL INSTRUMENT SYSTEM" and filed on Aug. 31, 2017. Chinese International Application No. PCT/CN2017/099918 claims priority to the priorities of Chinese Patent Application No. 201610797612.7 filed on Aug. 31, 2016, and Chinese patent application No. 201610798123.3 filed on Aug. 31, 2016. The entire contents of each of the above-identified applications are incorporated herein by reference for all purposes.

TECHNICAL FIELD

The present application relates to a flexible surgical instrument system, which belongs to the field of medical instruments.

BACKGROUND ART

In the single-port laparoscopic surgery and the natural orifice transluminal non-invasive surgery, all surgical instruments including a visual illumination module and a surgical manipulator have access to a surgical site through a single channel. A distal structure of a surgical instrument may consist of multiple rods hinged in series, and is driven by a pulling force from a steel wire rope, so that the surgical instrument can be turned at an articulated joint. Since the steel wire rope has to be continuously tensioned by a pulley, this driving method has difficulty in further miniaturization of the surgical instrument, and also in further improvement of the moving performance of the instrument.

SUMMARY OF THE INVENTION

Aiming at the above problems, an object of the present application is to provide a flexible surgical instrument system that can be better applied to a surgical robot system that passes through a natural orifice of human body or a single surgical incision and performs an operation.

In order to achieve the above object, the present application provides the following technical solutions. According to a first aspect of the present application, provided is a flexible surgical instrument system comprising a flexible surgical instrument, the flexible surgical instrument comprising a flexible continuous body structure composed of a distal structural body, a proximal structural body and a middle connecting body, wherein the distal structural body comprises at least one distal structural segment, and the distal structural segment comprises distal spacing disks, a distal fixing disk and structural backbones; the proximal structural body comprises a proximal structural segment, and the proximal structural segment comprises proximal spacing disks, a proximal fixing disk and structural backbones; the middle connecting body comprises channel fixing plates and a structural backbone guide channel provided between the channel fixing plates; and the structural backbones of the distal structural segment are securely connected, in one-to-one correspondence, to or are the same as the structural backbones of the proximal structural segment, one end of each of the structural backbones is securely connected to the proximal fixing disk, and the other end of the structural backbone passes through the proximal spacing disks, the structural backbone guide channel and the distal spacing disks in sequence, and is then securely connected to the distal fixing disk.

In an embodiment, the flexible surgical instrument system further comprises a driving unit. The driving unit comprises a driving unit fixing plate, a plurality of driving shafts are rotatably supported between the driving unit fixing plate and the channel fixing plate close to the proximal structural segment, the front end of each of the driving shafts is provided with a cable pulling mechanism, the cable pulling mechanism is securely connected to a cable fixing block by a cable passing through the proximal spacing disks and the proximal fixing disk, and the cable fixing block is securely connected to the proximal fixing disk; and when the driving shaft rotates, the length of the cable in the proximal structural segment is changed by the cable pulling mechanism.

In an embodiment, the cable pulling mechanism comprises a driving pulley, a driven pulley and the cable; and the driving pulley is securely sheathed over the driving shaft, one end of the cable is securely connected to the driving pulley, and the other end of the cable winds around the driven pulley and then threads into the proximal structural segment.

In an embodiment, the front end of the proximal structural segment is securely connected to the channel fixing plate; and a channel support plate is provided in front of the channel fixing plate on the side close to the proximal structural body, and the driven pulley is rotatably supported between the channel support plate and the channel fixing plate.

In an embodiment, a restraint structural backbone is provided inside the proximal structural segment, one end of the restraint structural backbone is securely connected to the channel fixing plate close to the proximal structural segment, and the other end is directly or indirectly connected to the proximal fixing disk, so as to keep the length of the proximal structural segment unchanged while turning.

In an embodiment, the flexible surgical instrument system further comprises a driving unit. The driving unit comprises a driving unit fixing plate, a plurality of driving shafts are rotatably supported between the driving unit fixing plate and the channel fixing plate close to the proximal structural segment, the front end of each of the driving shafts is provided with a cable pulling mechanism, the cable pulling mechanism is securely connected to a cable fixing block by a cable passing through the proximal spacing disks and the proximal fixing disk, and the cable fixing block is securely connected to the proximal fixing disk; and when the driving shaft rotates, the length of the cable in the proximal structural segment is changed by the cable pulling mechanism.

In an embodiment, the cable pulling mechanism comprises a bevel gear pair, a pulley, a pulley base and the cable; one bevel gear of the bevel gear pair is coaxially and securely connected to the driving shaft, the other bevel gear of the bevel gear pair is coaxially and securely connected to the pulley, and the two bevel gears of the bevel gear pair mesh with each other; the pulley is rotatably supported on the pulley base, and the pulley base is securely connected to the channel fixing plate; and one end of the cable is securely connected to the pulley, and the other end of the cable threads into the proximal structural segment.

In an embodiment, a universal joint is provided in the center of the proximal structural segment, the front end of the universal joint passes through the channel fixing plate and is connected to a universal joint base, the universal joint base is securely connected to a channel support plate, and the channel support plate is provided in front of the channel fixing plate on the side close to the proximal structural body; the cable fixing block can slide along the axis of the universal joint, and can be connected at the rear end of the universal joint rotatably around the axis of the universal joint.

In an embodiment, the driving unit further comprises a motor part and a motion transmission part; the motor part comprises a motor fixing plate and a plurality of first motors securely connected to the motor fixing plate; the motion transmission part comprises a plurality of proximal structural segment turning transmission chains for converting a rotary output of one of the first motors into rotary motions opposite to each other of two first output shafts; and front ends of the two first output shafts are directly or indirectly connected to rear ends of a pair of the driving shafts to transfer rotary motions of the first output shafts to the driving shafts.

In an embodiment, the proximal structural segment turning transmission chain comprises a first input gear, a first output gear, an idle gear and the two first output shafts, wherein the first input gear is securely sheathed over one of the two first output shafts, the first output gear is securely sheathed over the other of the two first output shafts, and the two first output shafts are in transmission connection via an even number of idle gears; and the rear end of the first output shaft securely connected by the first input gear is securely connected to an output shaft of the first motor via a coupling.

In an embodiment, a sterile barrier is provided between the motion transmission part and the driving unit fixing plate, and the sterile barrier comprises a sterile barrier support plate, a sterile barrier cover securely connected to an outer periphery of the sterile barrier support plate, and a plurality of female couplings rotatably connected to the sterile barrier support plate; a sterile membrane is securely connected to the sterile barrier cover; the rear end of each of the driving shafts is securely sheathed with a second output gear, the second output gear meshes with a second input gear, and a gear shaft of the second input gear passes through the driving unit fixing plate and is securely connected to a first male coupling; the front end of each of the first output shafts is securely connected to a second male coupling; and the second male coupling is connected to the first male coupling via the female coupling.

In an embodiment, a cover plate is arranged at a front end of the motion transmission part, the front end of each of the first output shafts passes through the cover plate and is rotatably connected to the cover plate, and a first connecting pin seat is provided on the cover plate; and a second connecting pin seat configured to be quickly connected to the first connecting pin seat is provided on the sterile barrier support plate.

In an embodiment, a surgical end effector is provided at a front end of the distal structural body, and a surgical end effector actuation wire with one end connected to the surgical end effector passes through the distal structural body, the surgical end effector actuation wire being connected at the other end to a surgical end effector driving mechanism; the surgical end effector driving mechanism comprises a connection rod, a connection frame, a threaded rod and a nut; the front end of the connection rod is securely connected to the rear end of the surgical end effector actuation wire, and the rear end of the connection rod is securely connected to the front end of the connection frame; the rear end of the connection frame is securely connected to the threaded rod, the nut is fitted on the threaded rod, and the nut is rotatably connected to the driving unit fixing plate; and the motor part further comprises a second motor securely connected to the motor fixing plate, an output shaft of the second motor is securely connected to the rear end of a second output shaft via a coupling, the front end of the second output shaft is securely sheathed with a third input gear, the third input gear meshes with a third output gear, the third output gear is securely connected to a third output shaft, and the front end of the third output shaft is directly or indirectly connected to the nut, thereby transferring the rotary motion of the third output shaft to the nut and converting same into a linear motion of the connection frame.

In an embodiment, the flexible surgical instrument system further comprises a flexible surgical instrument housing and a motor part housing, wherein the proximal structural body and the middle connecting body are both located in the flexible surgical instrument housing; the channel fixing plates and the driving unit fixing plate are both securely connected to the flexible surgical instrument housing; the motor part and the motion transmission part are both located in the motor part housing; a cover plate is arranged at the front end of the motion transmission part, the cover plate being securely connected to the flexible surgical instrument housing via a sterile barrier; the cover plate and the motor fixing plate are both rotatably connected to the motor part housing; and an inner ring gear is securely connected to an inner wall of the motor part housing, a third motor is securely connected to the motor fixing plate, an output shaft of the third motor is securely connected to the rear end of a fourth output shaft via a coupling, the front end of the fourth output shaft is securely connected to a fourth input gear, and the fourth input gear meshes with the inner ring gear.

In an embodiment, the flexible surgical instrument system further comprises a flexible surgical instrument housing, a motor part housing and a linear module, wherein the proximal structural body and the middle connecting body are both located in the flexible surgical instrument housing; the channel fixing plates and the driving unit fixing plate are both securely connected to the flexible surgical instrument housing; the motor part and the motion transmission part are both located in the motor part housing; a cover plate is arranged at the front end of the motion transmission part, the cover plate being securely connected to the flexible surgical instrument housing via a sterile barrier; the linear module comprises a support, a fourth motor securely connected on the support, and a linear feed mechanism securely connected to an output shaft of the fourth motor; and an output end of the linear feed mechanism is securely connected to the motor part housing, and the fourth motor drives the motor part and the motion transmission part by means of the linear feed mechanism, to drive the flexible continuous body structure and a part, located in front of the sterile barrier, of the driving unit to perform a linear motion by means of the sterile barrier.

In an embodiment, the linear feed mechanism comprises: a lead screw rotatably connected to the support, the lead screw is sheathed with a slider which is threadedly fitted with the lead screw, a linear sliding groove is provided on the support, and the slider is slidably provided in the linear sliding groove; and the output shaft of the fourth motor is securely connected to the lead screw via a coupling.

In an embodiment, the number of proximal structural segments in the proximal structural body is equal to the number of distal structural segments in the distal structural body.

The present application adopts the above technical solutions, and has the following advantages: 1. in the present application, a flexible continuous body structure comprising a proximal structural body, a middle connecting body and a distal structural body is used as the main body and cooperates with a driving unit, wherein the distal structural body is linked to the proximal structural body via the middle connecting body, the driving unit is linked to the proximal structural body, and when the driving unit drives the proximal structural body to turn in any direction, the distal structural body correspondingly turns in the opposite direction, and a flexible surgical arm formed by the distal structural body and an envelope is thus capable of turning in any direction; 2. the distal structural body, the middle connecting body and the proximal structural body of the present application use a redundant structural backbone arrangement (the number of the structural backbones is more than three), which can improve the stability and load capacity of the system; 3. in the present application, a plurality of driving shafts are rotatably connected between a driving unit fixing plate and a channel fixing plate, the front end of the driving shaft is provided with a cable pulling mechanism, the cable pulling mechanism is connected to a cable fixing block fixedly connected at the rear end of a proximal fixing disk via a cable, and when the driving shaft rotates, the length of the cable in the proximal structural segment can be changed by the cable pulling mechanism, in addition, the cable fixing block is connected to the channel fixing plate via a restraint structural backbone or a universal joint, thus converting the pulling of the cable into a turning motion of the proximal structural segment, and also enabling the turning profile of the proximal structural segment to be approximately circular arc; 4. in the present application, a surgical end effector actuation wire of a surgical end effector passes through the distal structural body to a surgical end effector driving mechanism and is fixedly connected to a connection rod, a connection frame is fixedly connected to the connection rod, and the connection frame can be driven by a set of linear motion mechanisms to implement motion control over the surgical end effector; 5. in the present application, a motor part housing is further provided, the motor fixing plate and the motor part housing are connected in a rotatable manner, an inner ring gear is securely connected to an inner wall of the motor part housing, the motor part is provided with a motor which is securely connected to the motor fixing plate, the motor is connected to an output shaft via a coupling, one end of the output shaft is securely connected to an input gear which meshes with the inner ring gear, and the motor can thus drive the rotation of the parts, as a whole, of the system other than the motor part housing and the inner ring gear, so that the flexible surgical arm has an overall rotational freedom; 6. in the present application, since the flexible surgical instrument housing is connected to the motor part and the motion transmission part via a sterile barrier, thereby effectively isolating a sterilized part, such as the flexible surgical instrument, located in front of the sterile barrier from other unsterilized parts located behind the sterile barrier, and the feasibility of clinical surgery can be thus ensured; and 7. in the present application, a linear module is further provided, which is connected to the motor part housing and can drive the flexible surgical instrument, the driving unit and the sterile barrier to perform a linear motion, so that the flexible surgical arm also has a linear feed degree of freedom.

The flexible surgical instrument system of the present application can be applied to the single-port laparoscopic surgery, and can also be applied to the natural orifice transluminal non-invasive surgery.

DETAILED DESCRIPTION OF EMBODIMENTS

The technical solutions of the embodiments of the present application will be clearly and completely described below in conjunction with the accompanying drawings of the embodiments of the present application; and obviously, the embodiments described are merely some of, rather than all, the embodiments of the present application. On the basis of the embodiments of the present application, all the other embodiments obtained by those skilled in the art without any inventive effort shall fall within the scope of protection of the present application.

Figure 1:
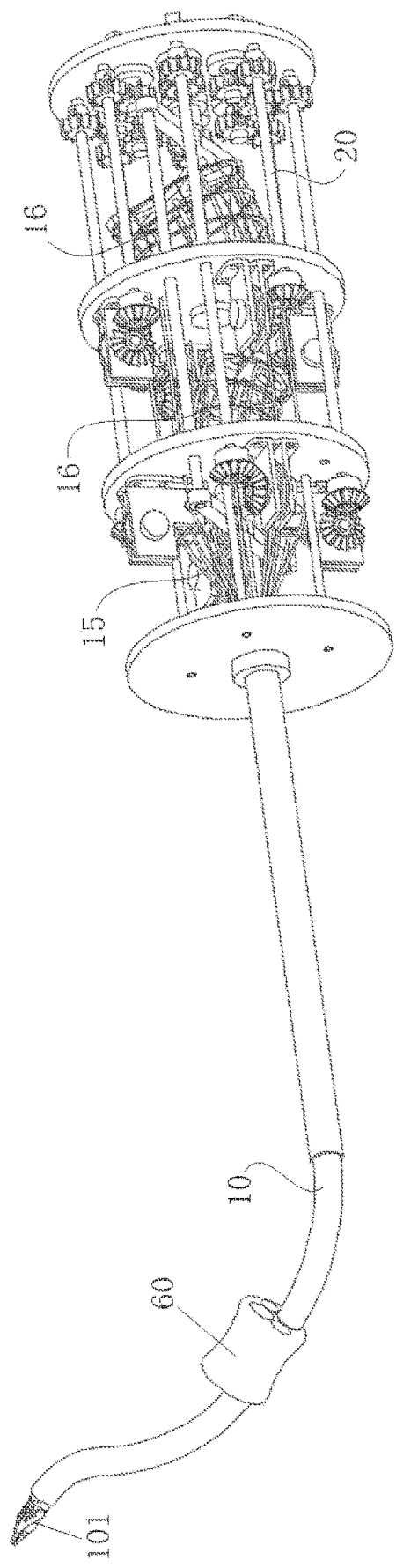
FIG. 1 is an overall structural schematic diagram of a flexible surgical instrument according to an example of the present application.

As shown in FIG. 1, a flexible surgical instrument system of the present application comprises a flexible surgical instrument 10 and a driving unit 20. Moreover, hereinafter, for a component, the distal end refers to the end of the component that is away from a surgical operator but close to a surgical site, and may also be referred to as the front end; and the proximal end refers to the end of the component that is close to the operator but away from the surgical site, and may also be referred to as the rear end.

Figure 2:
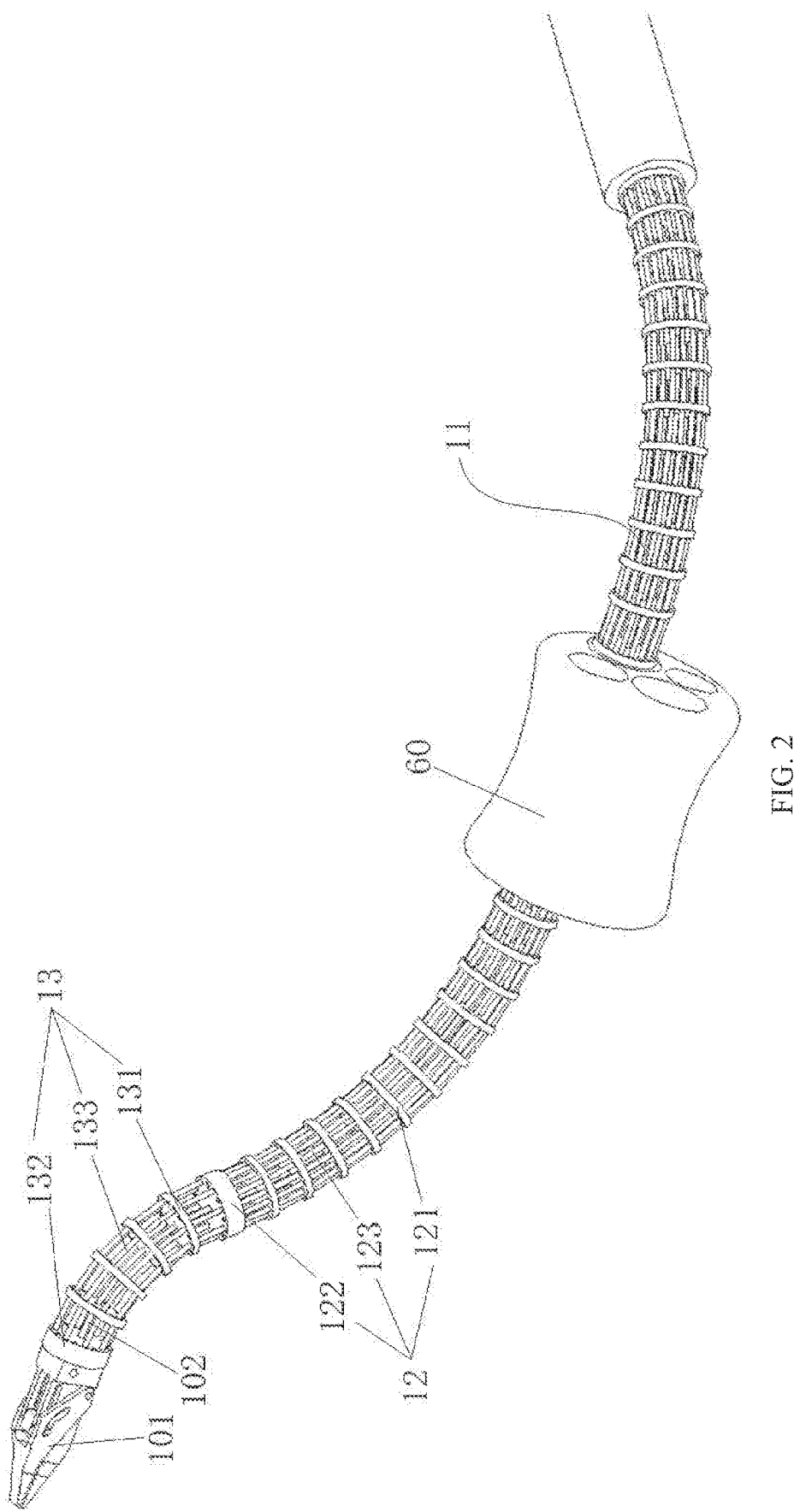
FIG. 2 is a structural schematic diagram of a distal structural body of a flexible surgical instrument according to an example of the present application.
Figure 3:
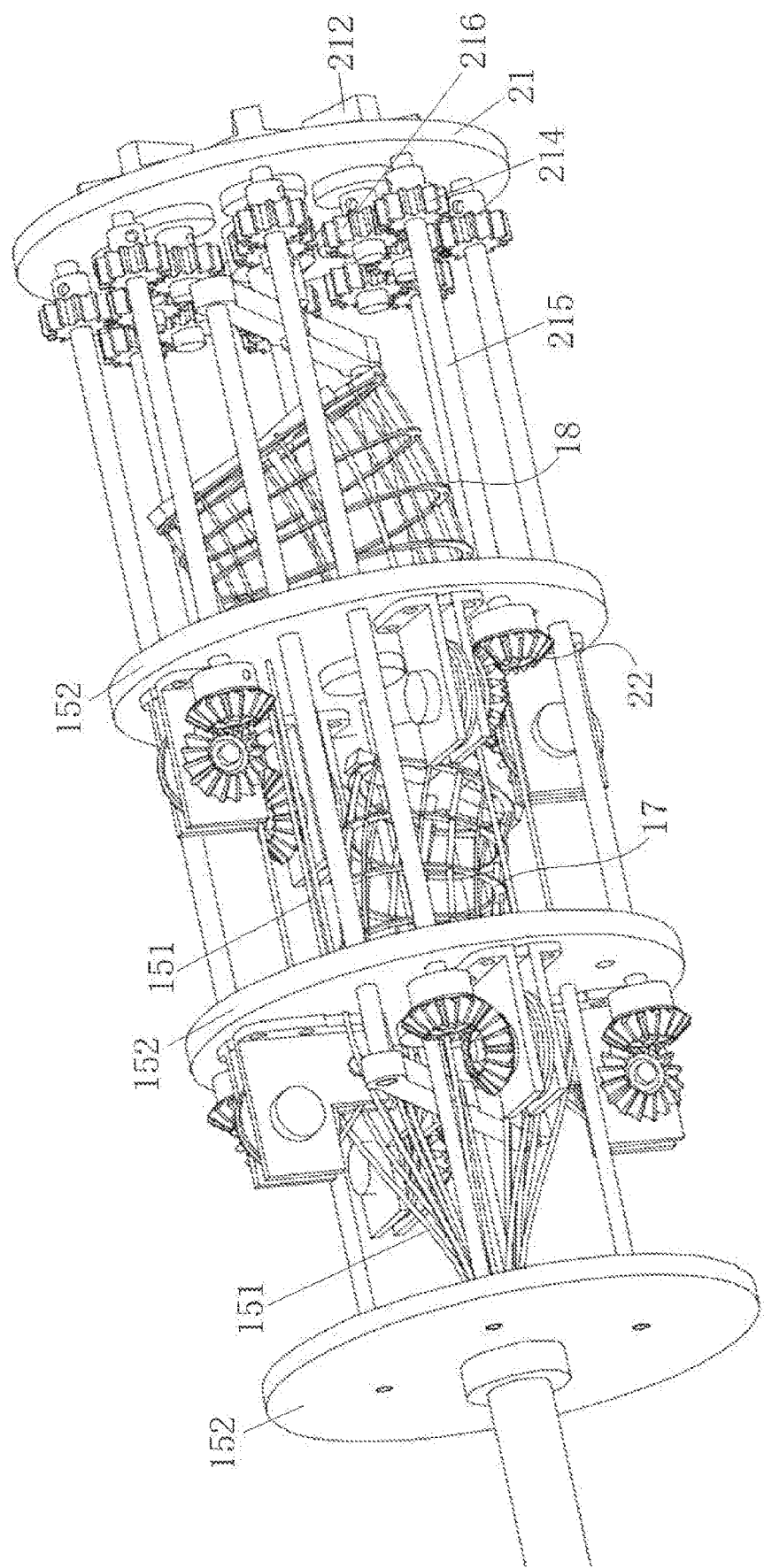
FIG. 3 is a structural schematic diagram of the flexible surgical instrument according to an example of the present application with the distal structural body omitted.

As shown in FIGS. 1 to 3, the flexible surgical instrument 10 comprises a flexible continuous body structure composed of a distal structural body 11, a proximal structural body 16 and a middle connecting body 15.

The distal structural body 11 comprises a first distal structural segment 12 and a second distal structural segment 13, wherein the first distal structural segment 12 comprises first distal spacing disks 121, a first distal fixing disk 122 and first segment structural backbones 123. The second distal structural segment 13 comprises second distal spacing disks 131, a second distal fixing disk 132 and second segment structural backbones 133. The first distal spacing disks 121 and the second distal spacing disks 131 are respectively distributed at intervals in the first distal structural segment 12 and the second distal structural segment 13, in order to prevent the first segment structural backbones 123 and the second segment structural backbones 133 from being destabilized when being pushed and pulled.

Figure 4:
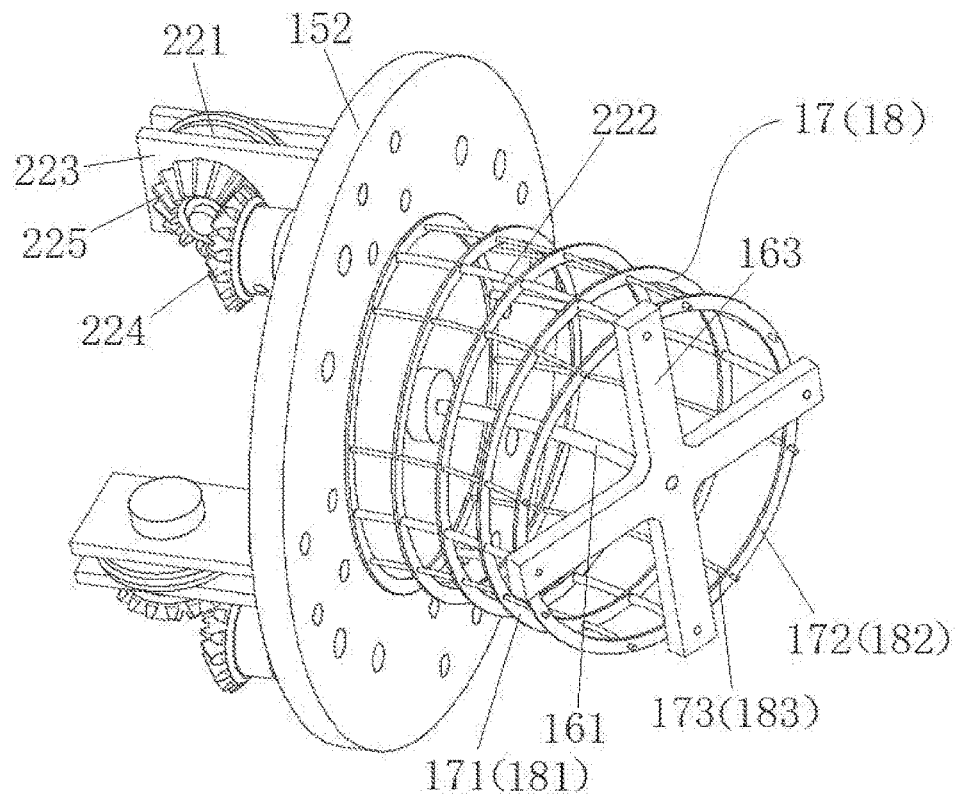
FIG. 4 is a structural schematic diagram of a proximal structural segment and a cable pulling mechanism according to an example of the present application.

The proximal structural body 16 comprises a first proximal structural segment 17 and a second proximal structural segment 18, as shown in FIG. 4, wherein the first proximal structural segment 17 comprises first proximal spacing disks 171, a first proximal fixing disk 172 and first segment structural backbones 173; and the second proximal structural segment 18 comprises second proximal spacing disks 181, a second proximal fixing disk 182, and second segment structural backbones 183. The first proximal spacing disks 171 and the second proximal spacing disks 181 are respectively distributed at intervals in the first proximal structural segment 17 and the second proximal structural segment 18, in order to prevent the first segment structural backbones 173 and the second segment structural backbones 183 from being destabilized when being pushed and pulled. The first segment structural backbones 173 of the first proximal structural segment 17 are securely connected, in one-to-one correspondence, to or are the same as the first segment structural backbones 123 of the first distal structural segment 12; and the second segment structural backbones 183 of the second proximal structural segment 18 are securely connected, in one-to-one correspondence, to or are the same as the second segment structural backbones 133 of the second distal structural segment 13. For each of the proximal structural segments 17, 18 or of the distal structural segments 12, 13, the number of structural backbones is three or more.

As shown in FIG. 3, the middle connecting body 15 comprises channel fixing plates 152 and structural backbone guide channels 151 securely connected between the channel fixing plates 152. One end of the first segment structural backbone 173 (123) is securely connected to the first proximal fixing disk 172, and the other end passes through the first proximal spacing disks 171, the structural backbone guide channel 151 and the first distal spacing disks 121 in sequence and is then securely connected to the first distal fixing disk 122. One end of the second segment structural backbone 183 (133) is securely connected to the second proximal fixing disk 182, and the other end passes through the second proximal spacing disks 181, the structural backbone guide channel 151, the first distal structural segment 12 and the second distal spacing disks 131 in sequence and is then securely connected to the second distal fixing disk 132. The structural backbone guide channel 151 functions to keep the shape of the first segment structural backbone 173 (123) and the second segment structural backbone 183 (133) unchanged when being subjected to a pushing or pulling force.

The number of the distal structural segments comprised in the distal structural body 11 and the number of the proximal structural segments comprised in the proximal structural body 16 mentioned above may also be one or more, but the number of the proximal structural segments is always consistent with the number of the distal structural segments. In addition, when the number of the distal structural segments is two or more, series connection may be used between the distal structural segments, for example, the second segment structural backbone 133 passes through the first distal fixing disk 122 and the first distal spacing disks 121, and if the first segment structural backbone 123 is of a tubular structure, the second segment structural backbone 133 can also pass through the first segment structural backbone 123. When the number of the proximal structural segments is two or more, series connection, independent arrangement or nested arrangement, etc. may be used between the structural segments. In this embodiment, as shown in FIG. 3, independent arrangement is used between two proximal structural segments. At this time, three channel fixing plates 152 are provided, the front end of the structural backbone guide channel 151 is securely connected to the channel fixing plate 152 on the side close to the distal structural body 11 to divide the structural backbone guide channel 151 into two parts, and the rear end of the structural backbone guide channel 151 is securely connected to other two channel fixing plates 152 and is used for guiding the first segment structural backbone 123 (173) and the second segment structural backbone 133 (183), respectively.

Figure 5:
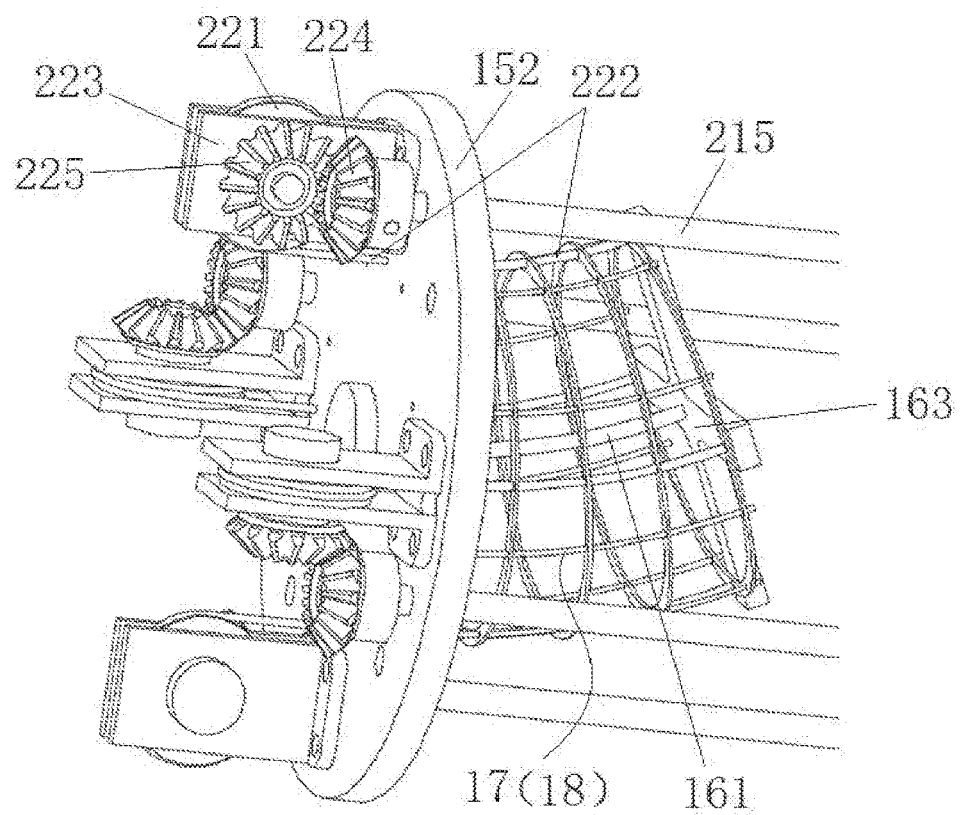
FIG. 5 is a schematic diagram of the proximal structural segment connected to the cable pulling mechanism as shown in FIG. 4 in another perspective.

As shown in FIGS. 3 to 5, the driving unit 20 comprises a driving unit fixing plate 21 and multiple driving shafts 215, some of the driving shafts 215 are rotatably supported between the driving unit fixing plate 21 and the channel fixing plate 152 in the rear position, other driving shafts 215 are rotatably supported between the driving unit fixing plate 21 and the channel fixing plate 152 in the middle, and the front end of the driving shaft 215 passes through the corresponding channel fixing plate 152. In this embodiment, eight driving shafts 215 are provided, and four driving shafts 215 are disposed between two channel fixing plates 152 and the driving unit fixing plate 21. The rear end of each driving shaft 215 is securely sheathed with an output gear 214, the output gear 214 meshes with an input gear 216, and a gear shaft of the input gear 216 passes through the driving unit fixing plate 21 and then extends backward. The front end of the driving shaft 215 is provided with a cable pulling mechanism 22, the cable pulling mechanism 22 comprises a bevel gear pair (bevel gears 224, 225), a pulley 221, a pulley base 223 and a cable 222, wherein one bevel gear 224 of the bevel gear pair is coaxially and securely connected to the driving shaft 215, the other bevel gear 225 of the bevel gear pair is coaxially and securely connected to the pulley 221, the bevel gear 224 meshes with the bevel gear 225, the pulley 221 is rotatably supported on the pulley base 223, the pulley base 223 is fixedly connected to the channel fixing plate 152, one end of the cable 222 is securely connected to the pulley 221, and the other end of the cable 222 passes through the channel fixing plate 152 or passes through the first proximal spacing disks 171 and the first proximal fixing disk 172 and is then securely connected to a cable fixing block 163, or passes through the second proximal spacing disks 181 and the second proximal fixing disk 182 and is then securely connected to another cable fixing block 163. The cable fixing block 163 is fixedly connected to the rear end of the first proximal fixing disk 172 or the second proximal fixing disk 182. By means of rotating the driving shaft 215, the cable 222 can be pulled and the length of same in the first proximal structural segment 17 or the second proximal structural segment 18 can be adjusted.

A restraint structural backbone 161 is provided in the center of each of the first proximal structural segment 17 and the second proximal structural segment 18, one end of the restraint structural backbone 161 is securely connected to the channel fixing plate 152, and the other end is securely connected to the center of the cable fixing block 163. The restraint structural backbone 161 is flexible and can turn, such that the proximal structural segment 17, 18 turns in an approximately circular arc shape under the cooperative driving of the cable 222, and then when the first (second) proximal structural segment 17 (18) turns in a certain direction, the first (second) distal structural segment 12 (13) will turn in the opposite direction in a certain proportional relationship (determined jointly by the distribution radii of the first (second) segment structural backbone 173 (183) and the first (second) segment structural backbone 123 (133)).

Figure 6:
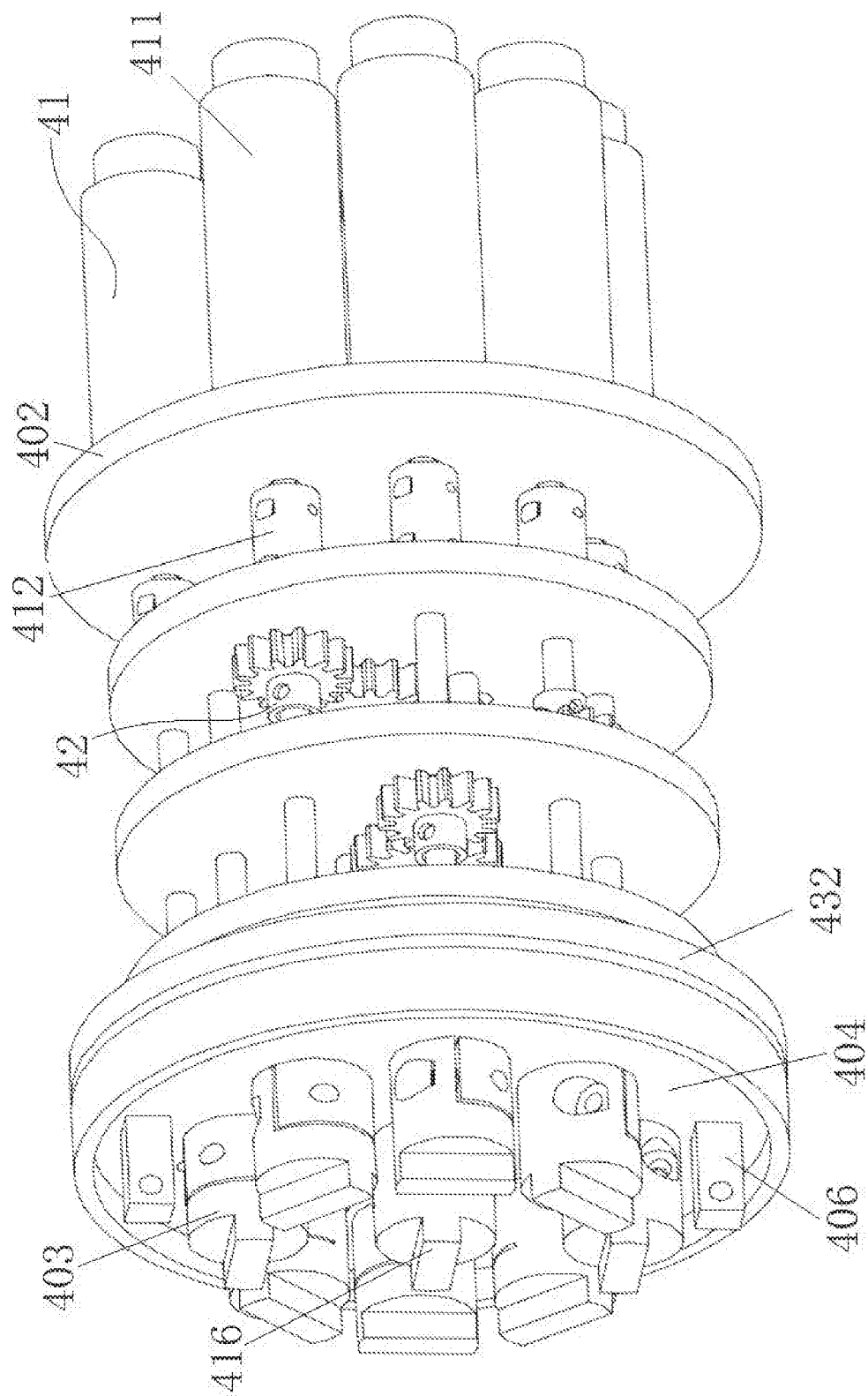
FIG. 6 is a structural schematic diagram of a motor part and a motion transmission part according to an example of the present application.
Figure 7:
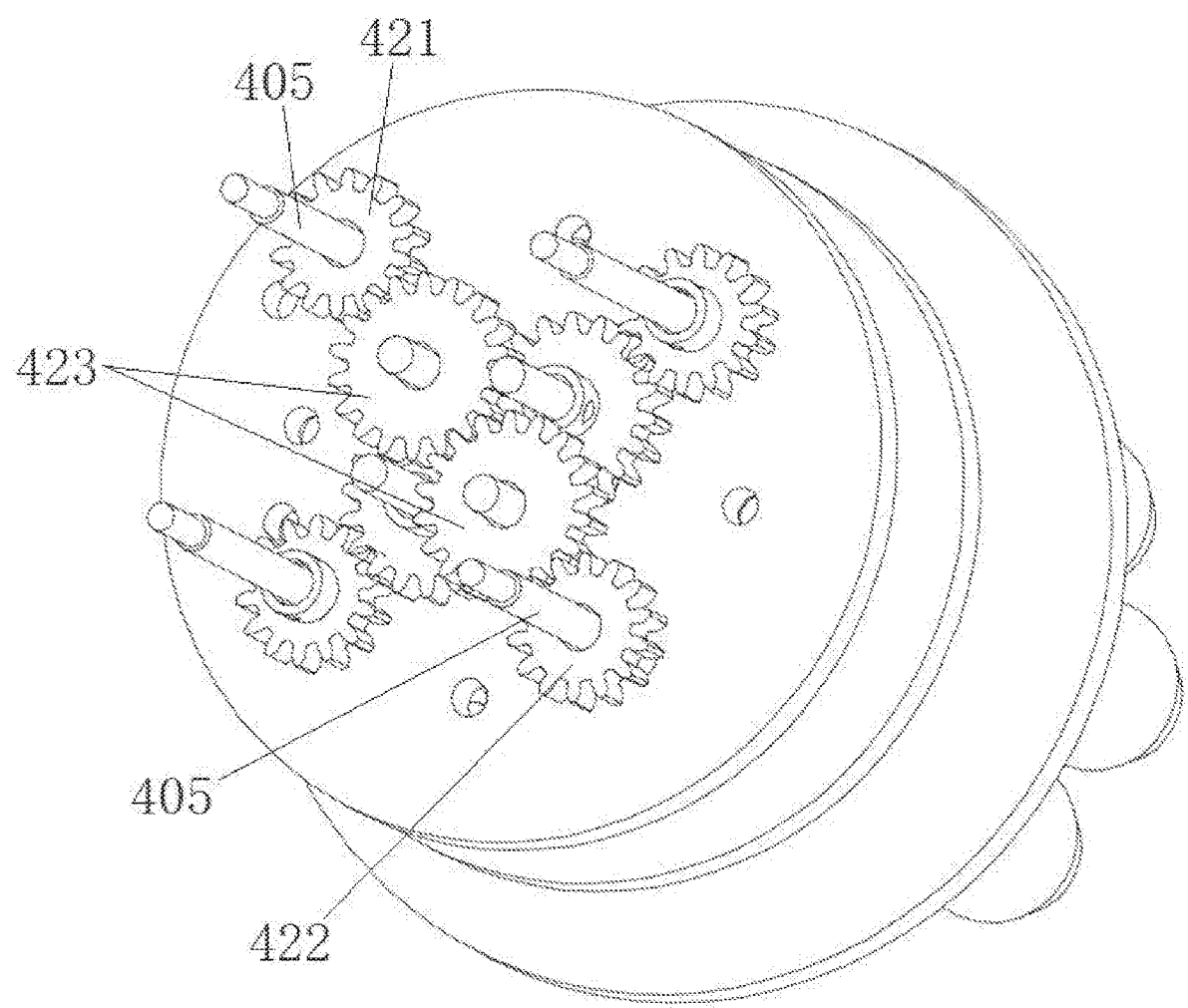
FIG. 7 is a structural schematic diagram of a proximal structural segment turning transmission chain according to an example of the present application.

In the above embodiment, as shown in FIG. 6 and FIG. 7, the driving unit 20 further comprises a motor part 41 and a motion transmission part. The motor part 41 comprises a motor fixing plate 402 and a plurality of first motors 411 securely connected to the motor fixing plate 402. The motion transmission part comprises a plurality of proximal structural segment turning transmission chains 42, each proximal structural segment turning transmission chain 42 is connected to an output shaft of one first motor 411 via a coupling 412 for decomposing the rotary output of the one first motor 411 into rotary motions opposite to each other of two output shafts 405, so as to transfer same to a pair of driving shafts 215 to achieve the cooperative loosening and tensioning of the cable fixing block 163. The proximal structural segment turning transmission chain 42 comprises an input gear 421, an output gear 422, two (which may also be another even number) idle gears 423, and two output shafts 405, wherein the input gear 421 is securely sheathed on one of the output shafts 405, and the rear end of the output shaft 405 is connected to the output shaft of the first motor 411 via the coupling 412; and the output gear 422 is securely sheathed on the other output shaft 405, and the input gear 421 is in transmission connection with the output gear 422 via the two (even number) idle gears 423. The front end of each output shaft 405 is directly or indirectly connected to the gear shaft of the input gear 216, whereby the two driving shafts 215 can be driven by the rotary output of the one first motor 411 (the two driving shafts 215 rotating opposite to each other), thereby driving the first proximal structural segment 17 or the second proximal structural segment 18 to turn in a certain direction.

Figure 8:
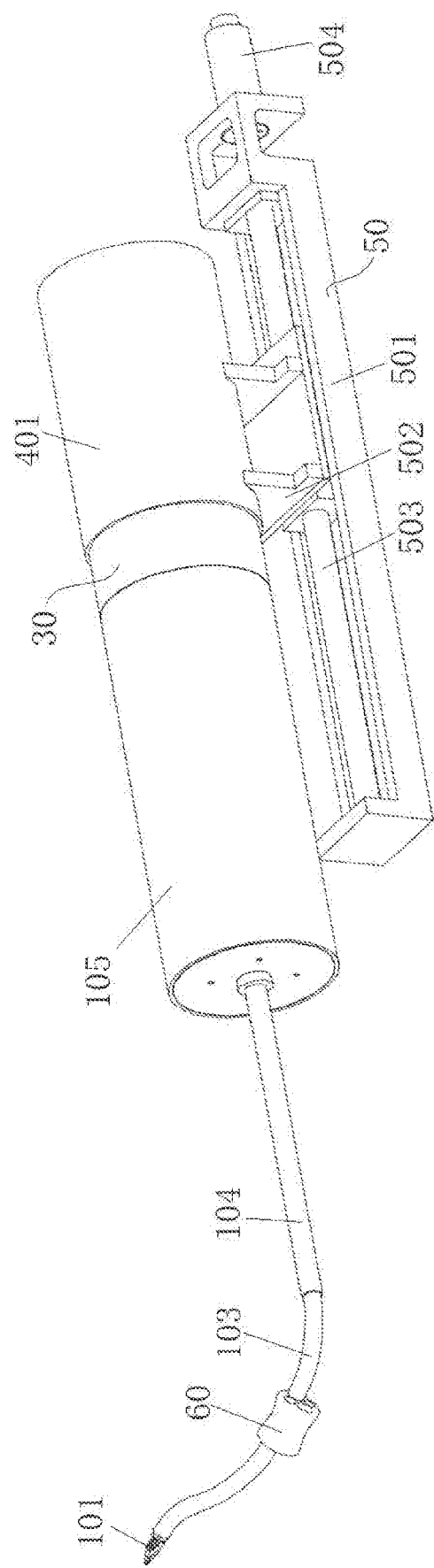
FIG. 8 is a structural schematic diagram of the flexible surgical instrument assembled with a flexible surgical instrument housing, a motor part housing, a sterile barrier and a linear module according to an example of the present application.
Figure 9:
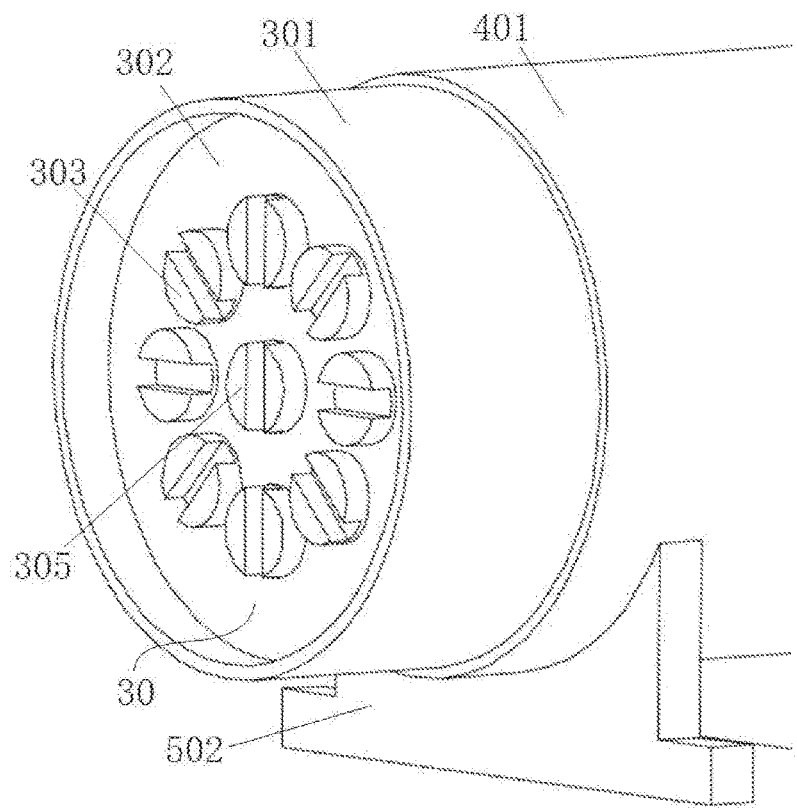
FIG. 9 is a structural schematic diagram of the sterile barrier connected to a cover plate according to an example of the present application.
Figure 10:
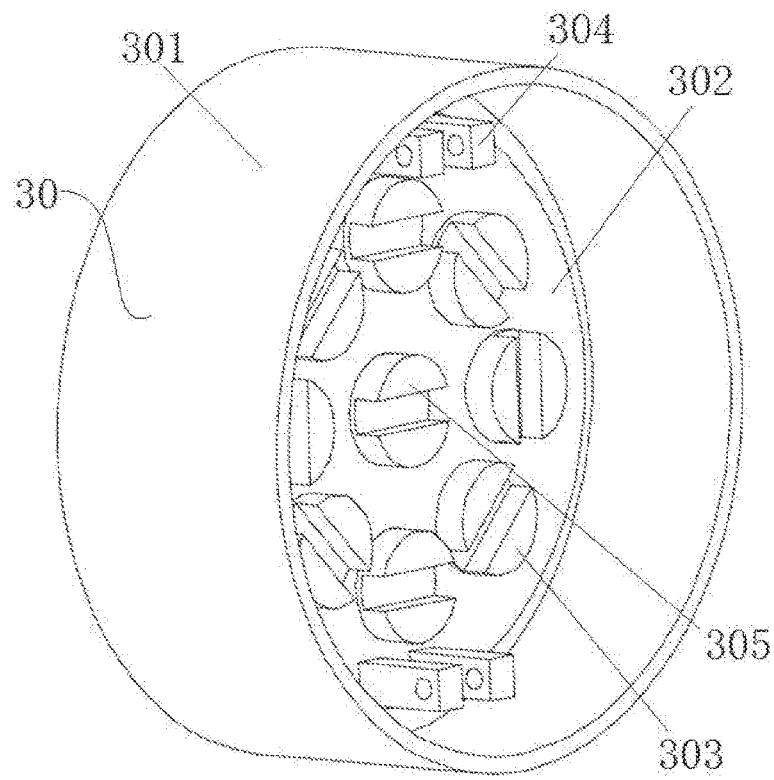
FIG. 10 is a structural schematic diagram of the sterile barrier according to an example of the present application in another perspective.

In the above embodiment, as shown in FIGS. 8 to 10, a sterile barrier 30 is provided between the motion transmission part and the driving unit fixing plate 21, and the sterile barrier 30 comprises a sterile barrier support plate 302, a sterile barrier cover 301 securely connected to an outer periphery of the sterile barrier support plate 302, and a plurality of female couplings 303 rotatably connected to the sterile barrier support plate 302. A first male coupling 212 (as shown in FIG. 3) configured to be connected to the female coupling 303 is securely connected to the rear end of the gear shaft of each input gear 216; A second male coupling 403 (as shown in FIG. 6) configured to be connected to the female coupling 303 is securely connected to the front end of each output shaft 405. The rotary motion of the output shaft 405 can thus be transferred to the driving shaft 215 via the second male coupling 403, the female coupling 303, the first male coupling 212, the input gear 216 and the output gear 214. A sterile membrane (not shown) is securely connected to the sterile barrier cover 301, which can isolate a sterilized part such as the flexible surgical instrument 10 that is located in front of the sterile barrier 30 from unsterilized parts such as the motion transmission part and the motor part 41 behind the sterile barrier 30, to ensure the feasibility of clinical surgery.

In the above embodiment, as shown in FIGS. 6 and 10, a cover plate 404 is arranged at the front end of the motion transmission part, the front end of each output shaft 405 passes through the cover plate 404 and is rotatably connected to the cover plate 404, and two sets of first connecting pin seats 406 are provided on the cover plate 404; and correspondingly, two sets of second connecting pin seats 304 configured to be quickly connected to the first connecting pin seats 406 are also provided on the sterile barrier support plate 302. In this way, the sterile barrier 30 is fixedly connected to the motion transmission part and can transfer the overall motion.

Figure 11:
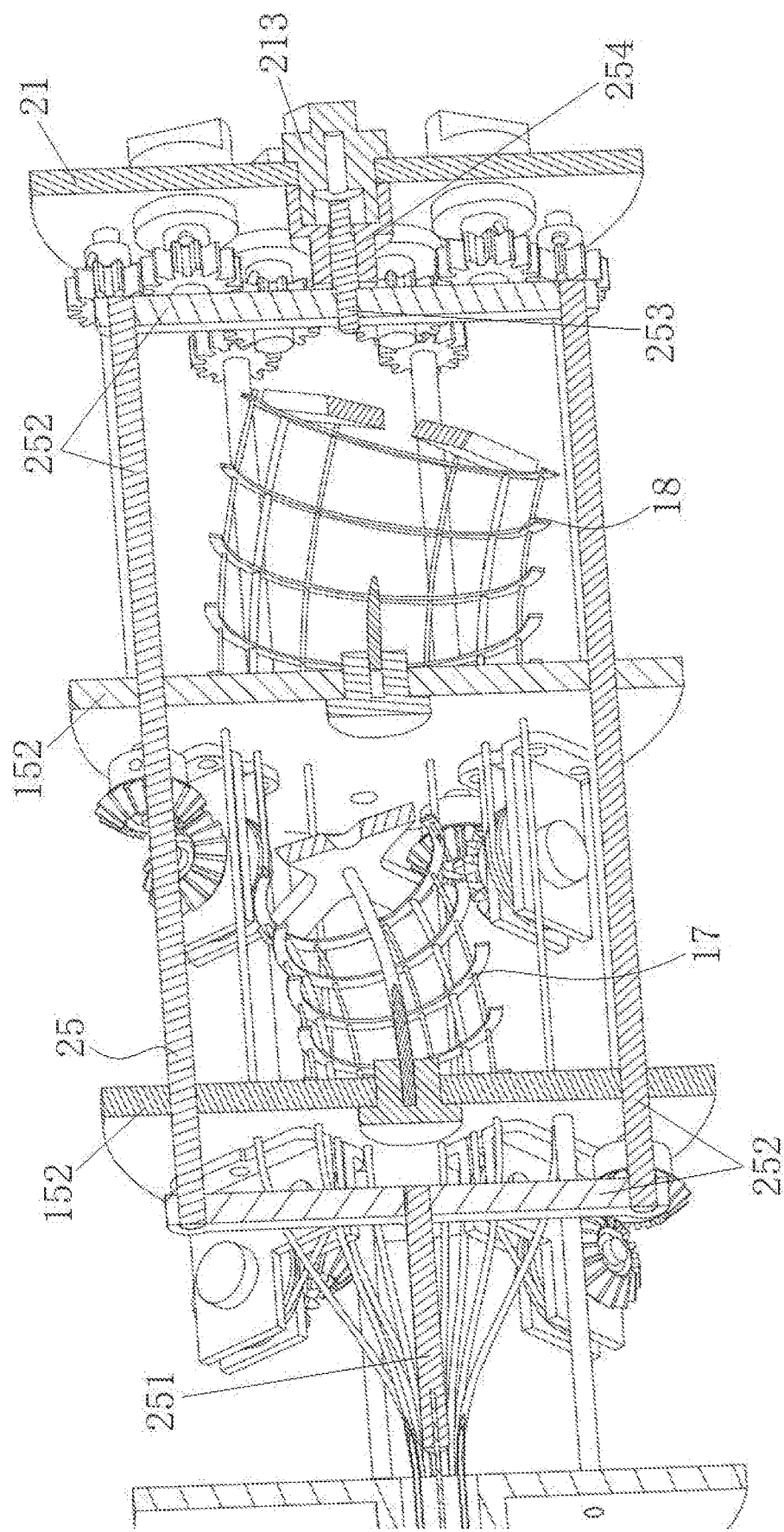
FIG. 11 is a structural schematic diagram of a longitudinal section of the flexible surgical instrument according to an example of the present application with the distal structural body omitted.
Figure 12:
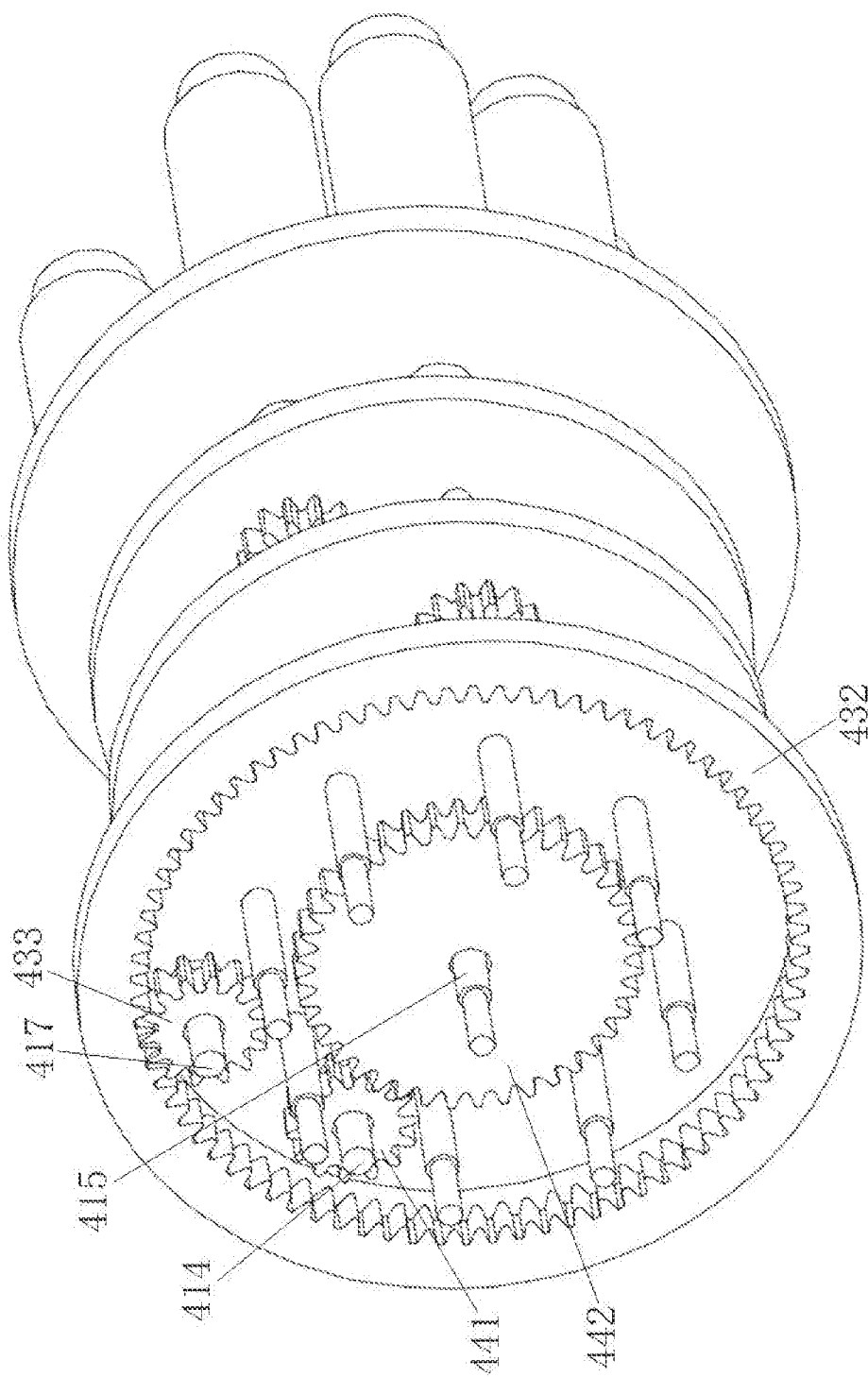
FIG. 12 is a structural schematic diagram of a rotary driving mechanism of the flexible surgical instrument according to an example of the present application.

In the above embodiment, as shown in FIGS. 2, 11 and 12, a surgical end effector 101 is provided at the front end of the distal structural body 11, and a surgical end effector actuation wire 102 connected at the distal end to the surgical end effector 101 passes through the distal structural body 11, and the proximal end of the surgical end effector actuation wire 102 is connected to a surgical end effector driving mechanism 25. The surgical end effector driving mechanism 25 comprises a connection rod 251, a connection frame 252, a threaded rod 253 and a nut 254, wherein the connection frame 252 is of a rigid rectangular frame structure and passes through the two channel fixing plates 152; and the front end of the connection rod 251 is securely connected to the rear end of the surgical end effector actuation wire 102, the rear end of the connection rod 251 is securely connected to the front end of the connection frame 252, the rear end of the connection frame 252 is securely connected to the threaded rod 253, the nut 254 is connected, in a matching manner, to the threaded rod 253, and the nut 254 is rotatably connected to the driving unit fixing plate 21. A second motor is securely connected to the motor fixing plate 402, an output shaft of the second motor is securely connected to the rear end of an output shaft 414 via the coupling 412, an input gear 441 is securely sheathed on the front end of the output shaft 414, the input gear 441 meshes with an output gear 442, the output gear 442 is securely connected to an output shaft 415, and the front end of the output shaft 415 is directly or indirectly connected to the nut 254 (such as via the sterile barrier 30) to transfer the rotary output of the second motor to the nut 254, thereby converting same into the linear motion of the connection frame 252 via the threaded rod 253, so that the surgical end effector actuation wire 102 is pushed or pulled to control the surgical end effector 101 (e.g., surgical forceps) to perform actions. The surgical end effector actuation wire 102 may also transfer various forms of energy, such as electrical energy and high-frequency vibrations, to achieve specific surgical functions (e.g., electrocoagulation, and electric resection) of the surgical end effector 101. Further, the front end of the output shaft 415 is securely connected to a male coupling 416 (as shown in FIG. 6), a male coupling 213 is securely connected to the rear end of the nut 254, and the male coupling 416 is connected to the male coupling 213 via a female coupling 305 (as shown in FIGS. 9 and 10) located on the sterile barrier 30.

In the above embodiment, as shown in FIGS. 8 and 12, the present application further comprises a flexible surgical instrument housing 105 and a motor part housing 401. The proximal structural body 16, the middle connecting body 15, the parts of the driving unit 20 other than the motor part 41 and the motion transmission part, and the surgical end effector driving mechanism 25 are all located in the flexible surgical instrument housing 105; and the channel fixing plate 152 and the driving unit fixing plate 21 are both securely connected to the flexible surgical instrument housing 105. The motor part 41 and the motion transmission part are both located in the motor part housing 401; and the cover plate 404 at the front end of the motion transmission part is securely connected to the flexible surgical instrument housing 105 via the sterile barrier 30, so that the flexible surgical instrument 10 can rotate integrally with the motion transmission part and the motor part 41. The cover plate 404 and the motor fixing plate 402 are both rotatably connected to the motor part housing 401. An inner ring gear 432 is securely connected to an inner wall of the motor part housing 401, and a third motor is securely connected to the motor fixing plate 402. An output shaft of the third motor is connected to the rear end of an output shaft 417 via the coupling 412, the front end of the output shaft 417 is securely connected to an input gear 433, and the input gear 433 meshes with the inner ring gear 432. When the output shaft of the third motor rotates, the input gear 433 is driven to rotate, and the input gear 433 travels in a circumferential direction of the inner ring gear 432, thereby driving the rotation of the parts, as a whole, of the present application other than the motor part housing 401 and the inner ring gear 432, and achieving control over the roll angle of the surgical end effector 101.

In the above embodiment, as shown in FIG. 8, the present application further comprises a linear module 50 (the linear module 50 being also isolated from the sterilized parts via the sterile membrane), which comprises a support 501 with a linear sliding groove, a motor 504 securely connected to the support, and a linear feed mechanism securely connected to the motor 504, wherein an output end of the linear feed mechanism is securely connected to the motor part housing, and the motor 504 drives the motor part and the motion transmission part by means of the linear feed mechanism, to drive the flexible continuous body structure and a part, located in front of the sterile barrier, of the driving unit to perform a linear motion by means of the sterile barrier. In an embodiment, the linear feed mechanism comprises a lead screw 503 rotatably connected to the support 501, and the lead screw 503 is sheathed with a slider 502 which is threadedly fitted with the lead screw 503 and is slidably provided in the linear sliding groove. The motor 504 is provided at the rear end of the support 501, and an output shaft of the motor 504 is securely connected to the lead screw 503 via a coupling. The motor part housing 401 is fixedly connected to the slider 502. When the output shaft of the motor 504 rotates, the slider 502 linearly moves the driving unit 20, the sterile barrier 30 and the flexible surgical instrument 10 along the sliding groove, thereby achieving a feed degree of freedom of the distal structural body 11.

Figure 13:
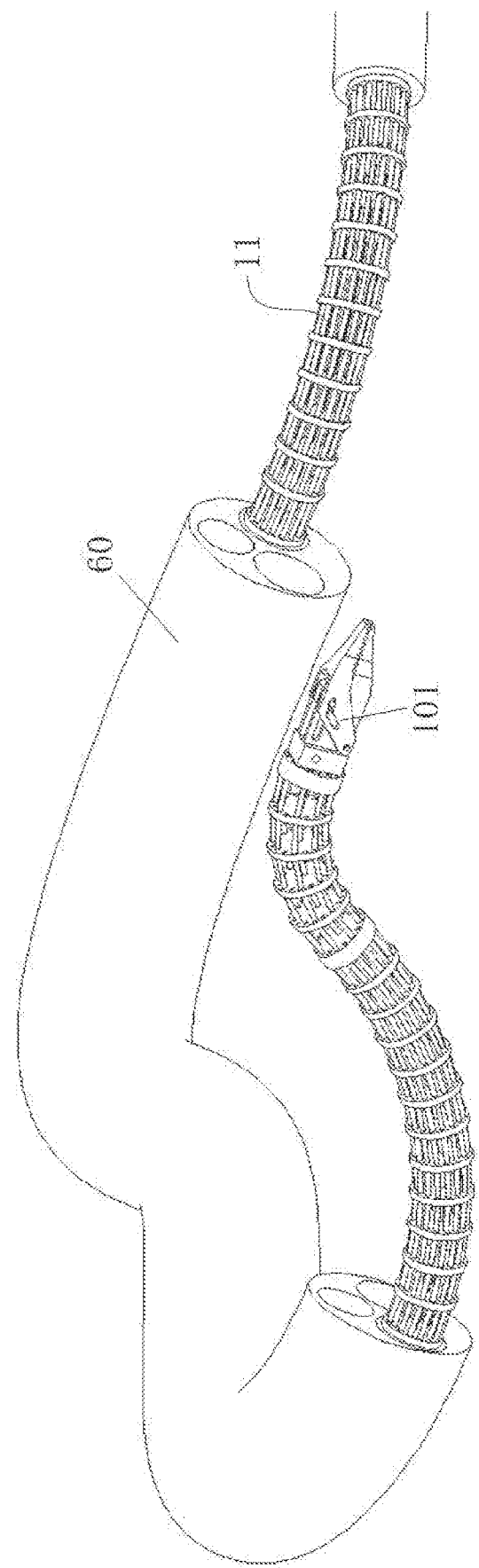
FIG. 13 is a structural schematic diagram of the distal structural body using a flexible sheath according to an example of the present application.
Figure 14:
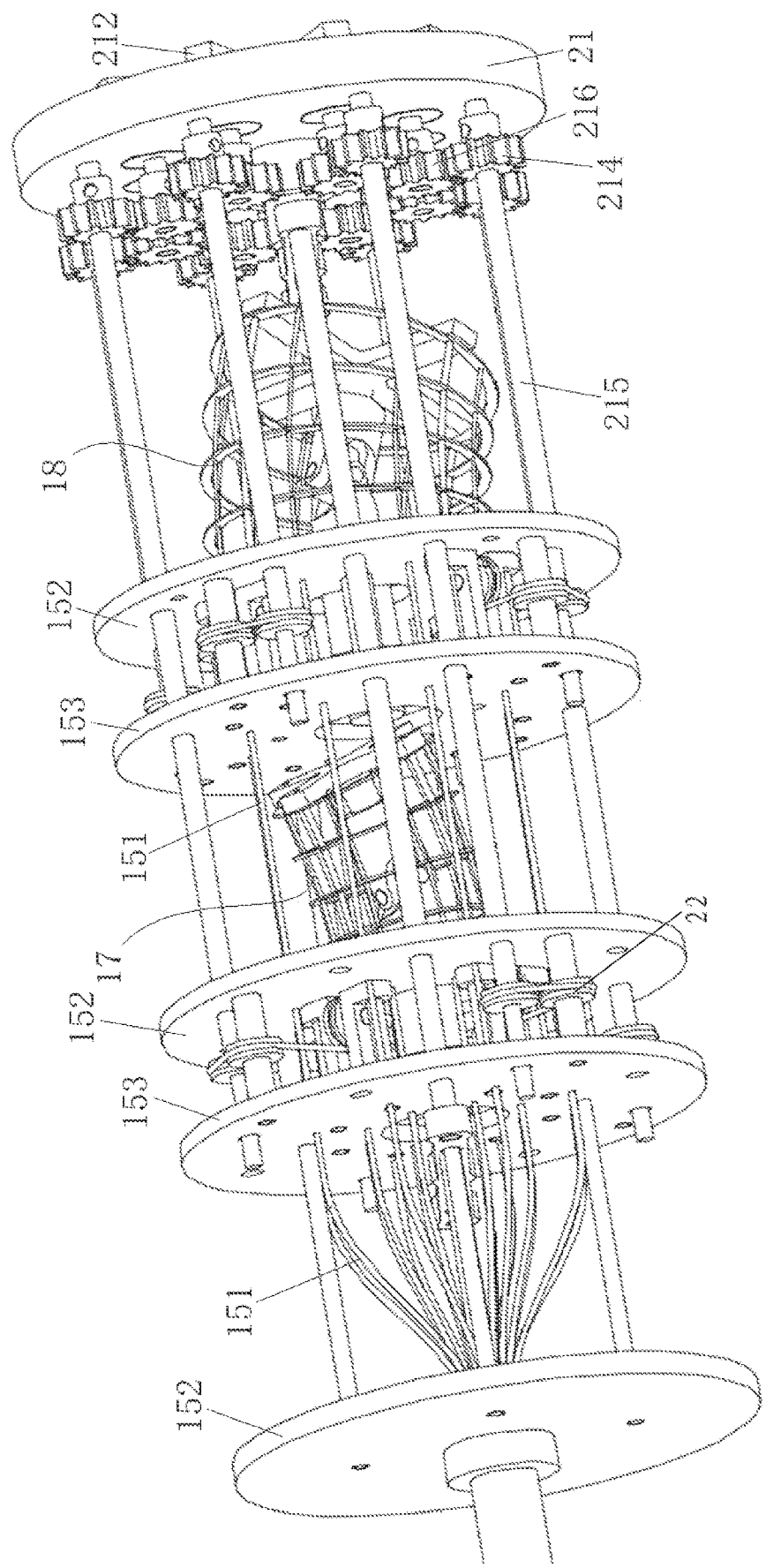
FIG. 14 is a structural schematic diagram of a flexible surgical instrument according to another example of the present application with a distal structural body omitted.
Figure 15:
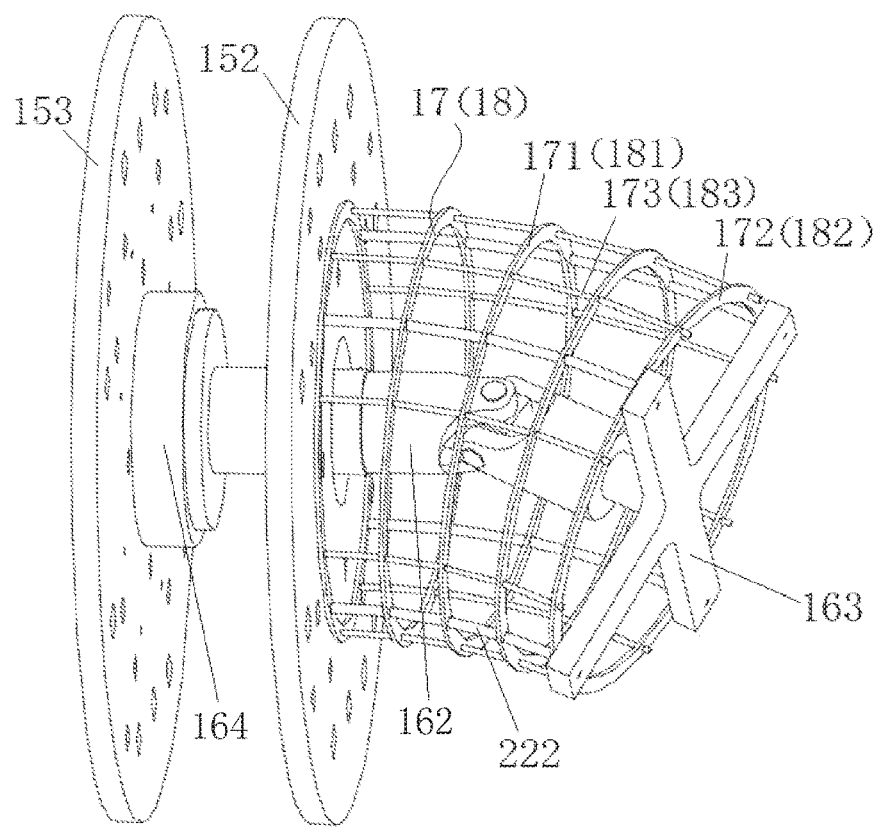
FIG. 15 is a structural schematic diagram of a proximal structural segment according to another example of the present application.
Figure 16:
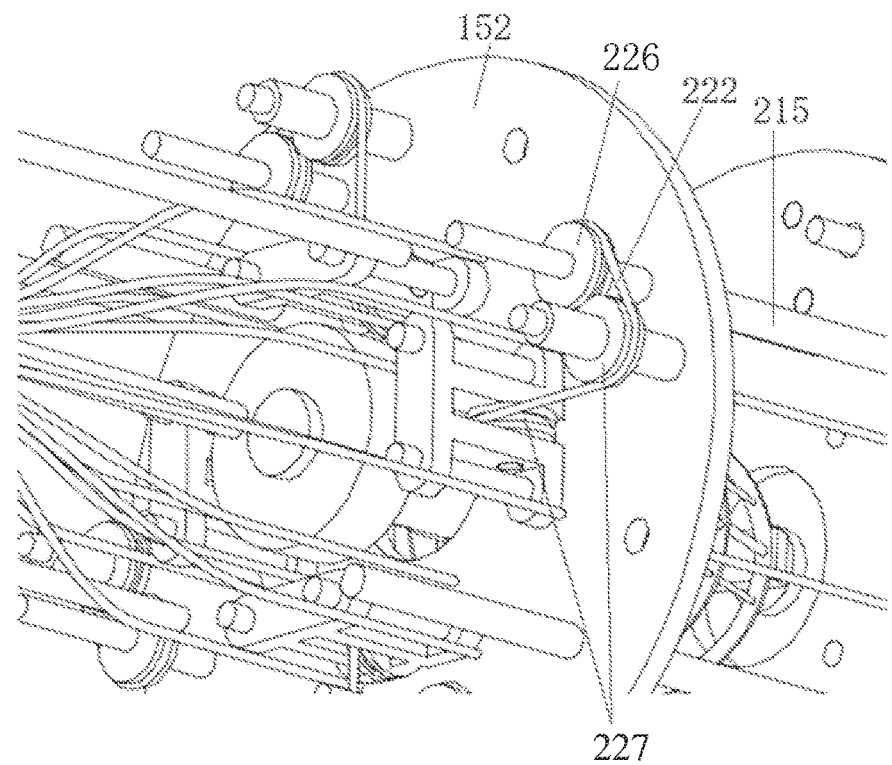
FIG. 16 is a structural schematic diagram of a cable pulling mechanism according to another example of the present application.
Figure 17:
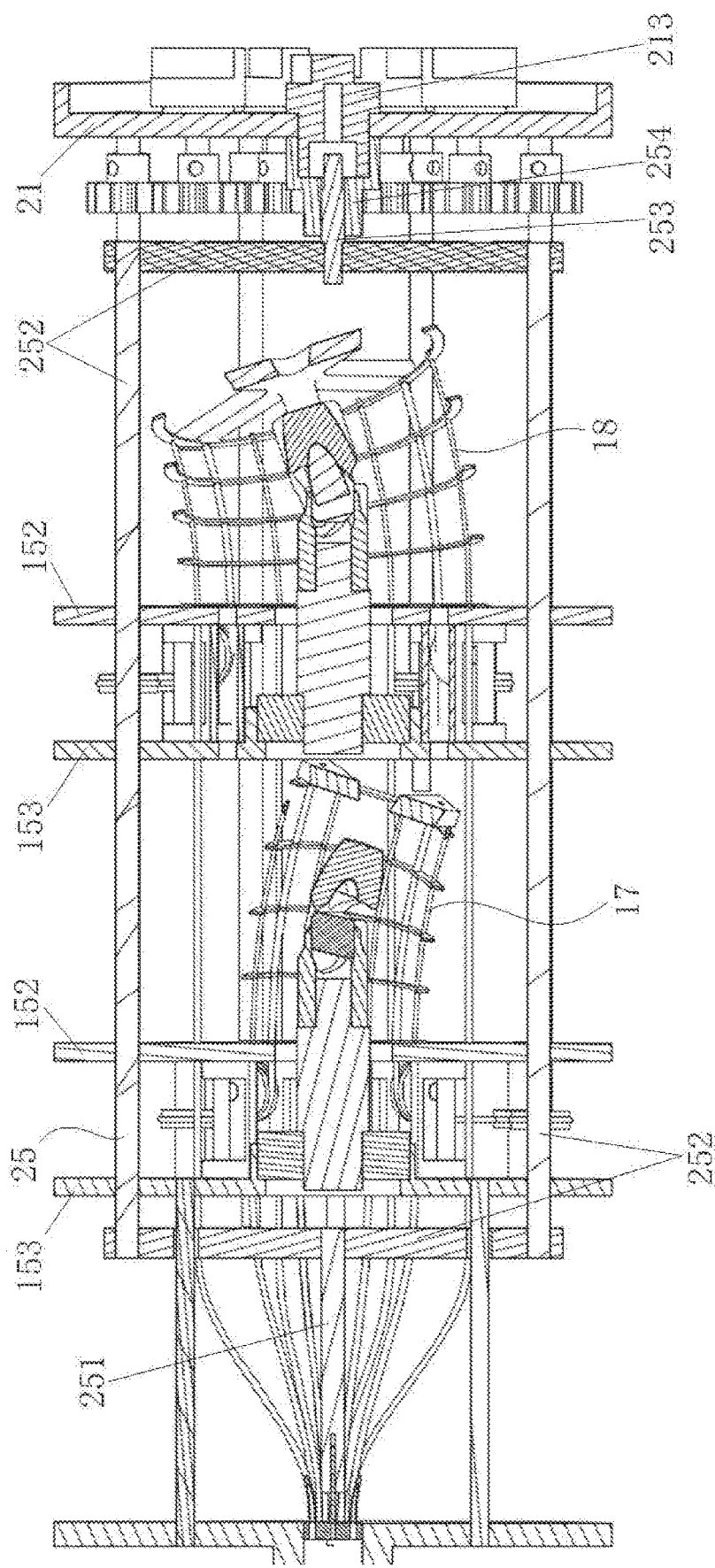
FIG. 17 is a structural schematic diagram of a surgical end effector driving mechanism according to another example of the present application.

In the above embodiment, as shown in FIG. 8, an envelope 103 is provided on the outside of the distal structural body 11 and functions to improve the smoothness of the distal structural body 11 entering a natural orifice or a surgical incision in the human body. A rigid outer sleeve 104 and a sheath 60 may also be provided on the outside of the envelope 103. In an application, the sheath 60 is fixed at a single incision in the abdominal cavity, and the distal structural body 11, together with the envelope 103 and the surgical end effector 101, can freely pass through a throughhole in the sheath 60 for the passage of the surgical instrument and have access to the surgical site to perform the single-port laparoscopic surgery. As shown in FIG. 13, the sheath 60 may also be a flexible sheath that can more easily extend into various natural orifices of the human body and adaptively change shape as the shape of the orifices, one end of the flexible sheath is fixed at the entrance of the orifice, and the distal structural body 11, together with the envelope 103 and the surgical end effector 101, can also freely pass through a through-hole in the flexible sheath for the passage of the surgical instrument and have access to the surgical site to perform non-invasive surgery through the natural orifice.

In another embodiment of the present application, as shown in FIGS. 14 to 17, the cable pulling mechanism 22 can comprise a driving pulley 226 securely sheathed over the driving shaft 215, the driving pulley 226 is securely connected to one end of the cable 222, and the other end of the cable 222 winds around two driven pulleys 227 or passes through the first proximal spacing disks 171 and the first proximal fixing disk 172 and is then securely connected to the cable fixing block 163, or passes through the second proximal spacing disks 181 and the second proximal fixing disk 182 and is then securely connected to another cable fixing block 163. By means of rotating the driving shaft 215, the cable 222 can be pulled and the length of same in the first proximal structural segment 17 or the second proximal structural segment 18 can be adjusted.

A universal joint 162 is provided in the center of each of the first proximal structural segment 17 and the second proximal structural segment 18, and the rear end of the universal joint 162 is slidably connected to a shaft-shaped feature in the front of the cable fixing block 163, that is, the shaft-shaped feature can slide along the axis in the rear end of the universal joint 162 and can rotate around the axis; and The front end of the universal joint 162 passes through the channel fixing plate 152 and is connected to a universal joint base 164, and the universal joint base 164 is securely connected to the channel support plate 153. In this embodiment, two channel support plates 153 are provided and are respectively provided in front of the channel fixing plate 152 on the side close to the proximal structural body. The universal joint 162 is provided such that the first proximal structural segment 17 and the second proximal structural segment 18 turns in an approximately circular arc shape. The length of the first proximal structural segment 17 and the second proximal structural segment 18 is restrained respectively by the first distal structural segment 12 and the second distal structural segment 13 via the first segment structural backbone 123 and the second segment structural backbone 133, and when the cable 222 is pulled, the corresponding proximal structural segment 17, 18 keeps the length unchanged along its axis while turning. By means of cooperatively controlling multiple cables 222, a plurality of degrees of freedom of the corresponding proximal structural segment 17, 18 can be achieved when turning in any direction, and in this embodiment, four degrees of freedom are provided. As an example of the second proximal structural segment 18, and when the cable 222 drives the second proximal structural segment 18 to turn in a certain direction, the second distal structural segment 13 will turn in the opposite direction in a certain proportional relationship (determined jointly by the distribution radii of the second segment structural backbone 183 in the second proximal structural segment 18 and the second segment structural backbone 133 in the second distal structural segment 13).

The front end of each of the first proximal structural segment 17 and the second proximal structural segment 18 is securely connected to the corresponding channel fixing plate 152, and the driven pulley 227 is rotatably supported between the channel support plate 153 and the channel fixing plate 152.

As shown in FIG. 8 and FIG. 12, the channel fixing plate 152, the channel support plate 153 and the driving unit fixing plate 21 are all securely connected to the flexible surgical instrument housing 105.

It should be noted that relational terms herein, such as first and second and the like, are used solely to distinguish one from another entity or action without necessarily requiring or implying any actual such relationship or order between such entities or actions. The terms "comprise," "include" or any variation thereof are intended to cover a non-exclusive inclusion, so that a process, method, article or apparatus that comprises a series of elements not only comprises those elements but also comprises other elements not expressly listed or inherent to such a process, method, article, or apparatus. In the absence of more restrictions, the element defined by the phrase "comprising a" does not preclude the presence of a further identical element in the process, method, article or apparatus that comprises the element.

The method and device provided in the embodiments of the present application have been described in detail, the principle and implementation of the present application have been illustrated with reference to the specific examples, and the above description of the embodiments is merely for the purpose of assisting in understanding the method of the present application and its core concept. For a person skilled in the art, various changes could also be made to the embodiments and the range of application in accordance with the concept of the present application. In summary, the contents of the description should not be construed as limiting the present application.

The invention claimed is:

1. A flexible surgical instrument system, comprising:
   a distal structural body comprising at least one distal structural segment each comprising a distal fixing disk and structural backbones;
   a proximal structural body comprising at least one proximal structural segment each comprising a proximal fixing disk, structural backbones, and driving backbones, the structural backbones of the at least one distal structural segment being securely connected in one-to-one correspondence to or the same as corresponding structural backbones of the at least one proximal structural segment;
   a plurality of cable pulling mechanisms operable to convert a rotational motion into a linear motion to turn the at least one proximal structural segment; and
   a driving unit to input the rotational motion to the plurality of cable pulling mechanisms;
   the driving unit comprising:
      a plurality of driving shafts operable to transfer the rotational motion to the plurality of cable pulling mechanisms, and a first end of each of the plurality of driving shafts is connected with each of the plurality of cable pulling mechanisms.

2. The flexible surgical instrument system of claim 1, wherein proximal ends of the structural backbones of the at least one proximal structural segment are securely connected to the at least one proximal fixing disk, and distal ends of the structural backbones of the at least one distal structural segment are securely connected to the at least one distal fixing disk.

3. The flexible surgical instrument system of claim 1, wherein the at least one proximal structural segment further comprises proximal spacing disks, the structural backbones of the at least one proximal structural segment passing through the proximal spacing disks; and
   wherein the at least one distal structural segment further comprises distal spacing disks, the structural backbones of the at least one distal structural segment passing through the distal spacing disks.

4. The flexible surgical instrument system of claim 1, wherein each of the plurality of cable pulling mechanisms comprises:
   a pulley part; and
   a cable comprising a first end securely connected to the pulley part and a second end securely connected to the at least one proximal fixing disk, and
   the pulley part is operable to convert the rotational motion into a linear motion of the second end of the cable, and change a length of the cable in the at least one proximal structural segment.

5. The flexible surgical instrument system of claim 4, wherein the pulley part comprises:
   a driving pulley to receive the rotational motion; and
   at least one driven pulley driven by the driving pulley and the cable in enwinding connection with the driven pulley.

6. The flexible surgical instrument system of claim 1, wherein each of the plurality of cable pulling mechanisms comprises:
   a gear-pulley part; and
   a cable comprising a first end securely connected to the gear-pulley part and a second end securely connected to the at least one proximal fixing disk, and
   the gear-pulley part is operable to convert the rotational motion into a linear motion of the second end of the cable, and change a length of the cable in the at least one proximal structural segment.

7. The flexible surgical instrument system of claim 6, wherein the gear-pulley part comprises:
   a gear pair at least comprising a first gear to receive the rotational motion and a second gear meshing with the first gear; and
   a pulley coaxially and securely connected to the second gear, and
   the cable is in enwinding connection with the pulley, and the first end of the cable is securely connected to the pulley.

8. The flexible surgical instrument system of claim 1, further comprising:
   a middle connecting body comprising channel fixing plates and structural backbone guide channels provided between the channel fixing plates, and
   the structural backbones of the at least one distal structural segment pass through the structural backbone guide channels and the distal ends of the structural backbones of the at least one distal structural segment are securely connected to the at least one distal fixing disk.

9. The flexible surgical instrument system of claim 8, further comprising:

a restraint structural backbone provided inside the at least one proximal structural segment, one end of the restraint structural backbone being securely connected to one of the channel fixing plates, and the other end being connected to the at least one proximal fixing disk.

10. The flexible surgical instrument system of claim 8, further comprising:
    a cable fixing block securely connected to the at least one proximal fixing disk;
    a universal joint base securely connected to one of the channel fixing plates; and
    a universal joint provided in a center of the at least one proximal structural segment and securely connected to the universal joint base and the cable fixing block.

11. The flexible surgical instrument system of claim 1, further comprising:
    a surgical end effector provided at a distal end of the distal structural body;
    a surgical end effector actuation wire passing through the distal structural body, the surgical end effector actuation wire comprising a proximal end securely connected to a surgical end effector driving mechanism and a distal end securely connected to the surgical end effector.

12. The flexible surgical instrument system of claim 1, wherein the driving unit comprises:
    a driving unit fixing plate.

13. The flexible surgical instrument system of claim 12, wherein the driving unit comprises:
    a motor part comprising a motor fixing plate and a plurality of first motors securely connected to the motor fixing plate; and
    a motion transmission part comprising a plurality of proximal segment turning transmission chains each operable to convert a rotational output of one of the plurality of first motors into mutually reversed rotational motions of two output shafts which transfer rotational motions to two of the plurality of driving shafts, respectively.

14. The flexible surgical instrument system of claim 13, wherein each of the plurality of proximal segment turning transmission chains comprises:
    an input gear securely sheathed over one of the two output shafts which is securely connected to the one of the plurality of first motors;
    an output gear securely sheathed over an other one of the two output shafts; and
    idle gears, the input gear being in transmission connection with the output gear via the idle gears.

15. The flexible surgical instrument system of claim 13, further comprising:
    a sterile barrier fixedly connected to the motion transmission part and provided between the cable pulling mechanisms and the motion transmission part.

16. The flexible surgical instrument system of claim 15, wherein the sterile barrier comprises:
    a sterile barrier support plate;
    a sterile barrier cover securely connected to an outer periphery of the sterile barrier support plate; and
    a plurality of couplings rotatably connected to the sterile barrier support plate.

17. The flexible surgical instrument system of claim 16, wherein the motion transmission part comprises:
    a cover plate arranged at a distal end of the motion transmission part; and
    a first connecting pin seat provided on the cover plate, and the sterile barrier support plate comprises a second connecting pin seat connected with the first connecting pin seat.

18. The flexible surgical instrument system of claim 13, further comprising:
    a flexible surgical instrument housing, the proximal structural body being located in the flexible surgical instrument housing;
    a motor part housing;
    a cover plate arranged at a distal end of the motion transmission part, the cover plate and the motor fixing plate being rotatably connected to the motor part housing and the cover plate being securely connected to the flexible surgical instrument housing via a sterile barrier,
    an inner ring gear securely connected to an inner wall of the motor part housing and meshing with an input gear, and
    a third motor securely connected to the motor fixing plate, an output shaft of the third motor being connected to a proximal end of a fourth output shaft, a distal end of the fourth output shaft being securely connected with the input gear.

19. The flexible surgical instrument system of claim 1, further comprising a linear module to drive the flexible surgical instrument and the driving unit to perform a linear motion.

* * * * *